(12) United States Patent
Ishimaru et al.

(10) Patent No.: US 10,011,129 B2
(45) Date of Patent: Jul. 3, 2018

(54) CONVEYANCE DETECTION APPARATUS, CONVEYING APPARATUS, AND RECORDING APPARATUS

(71) Applicant: CANON COMPONENTS, INC., Kodama-gun, Saitama (JP)

(72) Inventors: Masashi Ishimaru, Saitama (JP); Yoshihisa Negishi, Saitama (JP); Kenichi Matsumoto, Saitama (JP); Yoshihiro Hattori, Saitama (JP)

(73) Assignee: CANON COMPONENTS, INC., Saitama (JP)

( * ) Notice: Subject to any disclaimer, the term of this patent is extended or adjusted under 35 U.S.C. 154(b) by 0 days.

(21) Appl. No.: 15/618,411

(22) Filed: Jun. 9, 2017

(65) Prior Publication Data
US 2017/0355206 A1 Dec. 14, 2017

(30) Foreign Application Priority Data

Jun. 14, 2016 (JP) .................................. 2016-118127

(51) Int. Cl.
| | | |
|---|---|---|
| *B41J 13/00* | (2006.01) | |
| *B65H 7/14* | (2006.01) | |
| *B65H 5/06* | (2006.01) | |
| *G03G 15/00* | (2006.01) | |
| *B41J 11/00* | (2006.01) | |
| *G01N 21/86* | (2006.01) | |

(52) U.S. Cl.
CPC ....... *B41J 13/0009* (2013.01); *B41J 11/0095* (2013.01); *B65H 5/062* (2013.01); *B65H 7/14* (2013.01); *G01N 21/86* (2013.01); *G03G 15/6529* (2013.01)

(58) Field of Classification Search
CPC ........ B41J 29/02; B41J 19/08; B41J 13/0009; B41J 11/0095; H04N 1/00; B65H 7/00; B65H 5/062; B65H 7/14; H05K 5/02; G01N 21/86; G03G 15/6529
See application file for complete search history.

(56) References Cited

U.S. PATENT DOCUMENTS 8,303,074 B2 * 11/2012 Burke .................. B41J 11/0095
347/14

FOREIGN PATENT DOCUMENTS

JP 2007217176 A 8/2007

* cited by examiner

*Primary Examiner* — Thinh H Nguyen
(74) *Attorney, Agent, or Firm* — Rossi, Kimms & McDowell LLP (57) ABSTRACT

Provided is a control unit of a conveying apparatus, the conveying apparatus including: a conveying unit that conveys recording paper along a conveyance path; an imaging unit that images the recording paper; and a light emitting unit arranged on an opposite side of the imaging unit across the conveyance path, wherein the control unit detects conveyance information of the recording paper based on image information of the recording paper imaged by the imaging unit in a state in which light from the light emitting unit is transmitted through the recording paper. The control unit detects the conveyance information of the recording paper based on a plurality of images of the recording paper imaged at different timings by the imaging unit.

7 Claims, 7 Drawing Sheets

CONVEYANCE DETECTION APPARATUS, CONVEYING APPARATUS, AND RECORDING APPARATUS

CROSS-REFERENCE TO RELATED APPLICATIONS

This application is based upon and claims the benefit of priority of the prior Japanese Patent Application No. 2016-118127, filed on Jun. 14, 2016, the entire contents of which are incorporated herein by reference.

BACKGROUND OF THE INVENTION

Field of the Invention

The present invention relates to a conveyance detection apparatus, a conveying apparatus, and a recording apparatus.

Description of the Related Art

There is a known recording apparatus that conveys a recording medium while controlling an amount of conveyance and that records an image on the recording medium. A control apparatus disclosed in Patent Document 1 includes: an imaging apparatus arranged on a conveyance route of recording paper; and a conveyance amount calculation unit that calculates an amount of conveyance of the recording paper based on an image obtained by the imaging apparatus. The imaging apparatus includes a light emitting element and an image pickup element. The light emitting element emits light to the surface of the recording paper from obliquely above, and the image pickup element images a region on the recording paper illuminated by the light emitting element while the region is enlarged by an optical system. In this case, the image pickup element images minute undulations on the surface of the recording paper as a two-dimensional image. The conveyance amount calculation unit calculates an actual amount of conveyance of the recording paper from a moving distance of an image pattern on the photographed image.

In the control apparatus of Patent Document 1, the light emitting element emits light to the surface of the recording paper from obliquely above, and the light from the light emitting element is reflected in various directions due to unevenness on the surface of the recording paper. Therefore, focusing on a specific region of the recording paper, the position of the specific region before and after the conveyance is different when the recording paper is conveyed for a predetermined distance. Therefore, it is difficult to equalize the incident angle of the light going toward the image pickup apparatus after reflection of the light from the light emitting element. As a result, the image of the specific region of the recording paper changes before and after the conveyance for the predetermined distance, and the accuracy of calculating the amount of conveyance of the recording paper may be reduced.

Patent Document 1

Japanese Laid-Open Patent Publication No. 2007-217176

SUMMARY OF THE INVENTION

The present invention has been made in view of the problems, and an object of the present invention is to enable detecting highly accurate conveyance information.

The present invention provides a conveyance detection apparatus of a conveying apparatus, the conveying apparatus including: a conveying unit that conveys a conveyed object along a conveyance path; an imaging unit that images the conveyed object; and a light emitting unit arranged on an opposite side of the imaging unit across the conveyance path, the conveyance detection apparatus including a conveyance detection unit that detects conveyance information of the conveyed object based on image information of the conveyed object imaged by the imaging unit in a state in which light from the light emitting unit is transmitted through the conveyed object, wherein the conveyance detection unit detects the conveyance information of the conveyed object based on a plurality of images of the conveyed object imaged at different timings by the imaging unit.

The present invention provides a conveying apparatus including: a conveying unit that conveys a conveyed object along a conveyance path; an imaging unit that images the conveyed object; a light emitting unit arranged on an opposite side of the imaging unit across the conveyance path; a conveyance detection unit that detects conveyance information of the conveyed object based on image information of the conveyed object imaged by the imaging unit in a state in which light from the light emitting unit is transmitted through the conveyed object; and a housing that houses the conveying unit, the imaging unit, and the light emitting unit, wherein the conveyance detection unit detects the conveyance information of the conveyed object based on a plurality of images of the conveyed object imaged at different timings by the imaging unit.

The present invention provides a recording apparatus including: a conveying unit that conveys a conveyed object along a conveyance path; an imaging unit that images the conveyed object; a light emitting unit arranged on an opposite side of the imaging unit across the conveyance path; a conveyance detection unit that detects conveyance information of the conveyed object based on image information of the conveyed object imaged by the imaging unit in a state in which light from the light emitting unit is transmitted through the conveyed object; and a recording unit that records an image based on the conveyance information detected by the conveyance detection unit, wherein the conveyance detection unit detects the conveyance information of the conveyed object based on a plurality of images of the conveyed object imaged at different timings by the imaging unit.

DETAILED DESCRIPTION OF THE PREFERRED EMBODIMENTS

An embodiment of the present invention will now be described in detail with reference to the drawings.

The present embodiment provides a conveyance detection apparatus and a conveying apparatus or a recording apparatus including the conveyance detection apparatus. The conveyance detection apparatus detects conveyance information of a conveyed object. The conveying apparatus conveys the conveyed object based on the conveyance information of the conveyed object detected by the conveyance detection apparatus. The recording apparatus forms an image based on the conveyance information of the conveyed object, specifically, recording paper, detected by the conveyance detection apparatus and records the image.

In the following drawings, a conveyance direction of the conveyed object will be expressed as an X direction, a direction orthogonal to the X direction and parallel to a conveyed surface will be expressed as a Y direction, and a direction orthogonal to the conveyed surface will be expressed as a Z direction, as necessary. The side of a paper feeding opening 14 described later in the conveyance direction will be called an upstream, and the side of a paper discharge opening 15 described later will be called a downstream.

First Embodiment

A recording apparatus 100 according to the present embodiment is applied to an inkjet type printer in the following description.

Figure 1:
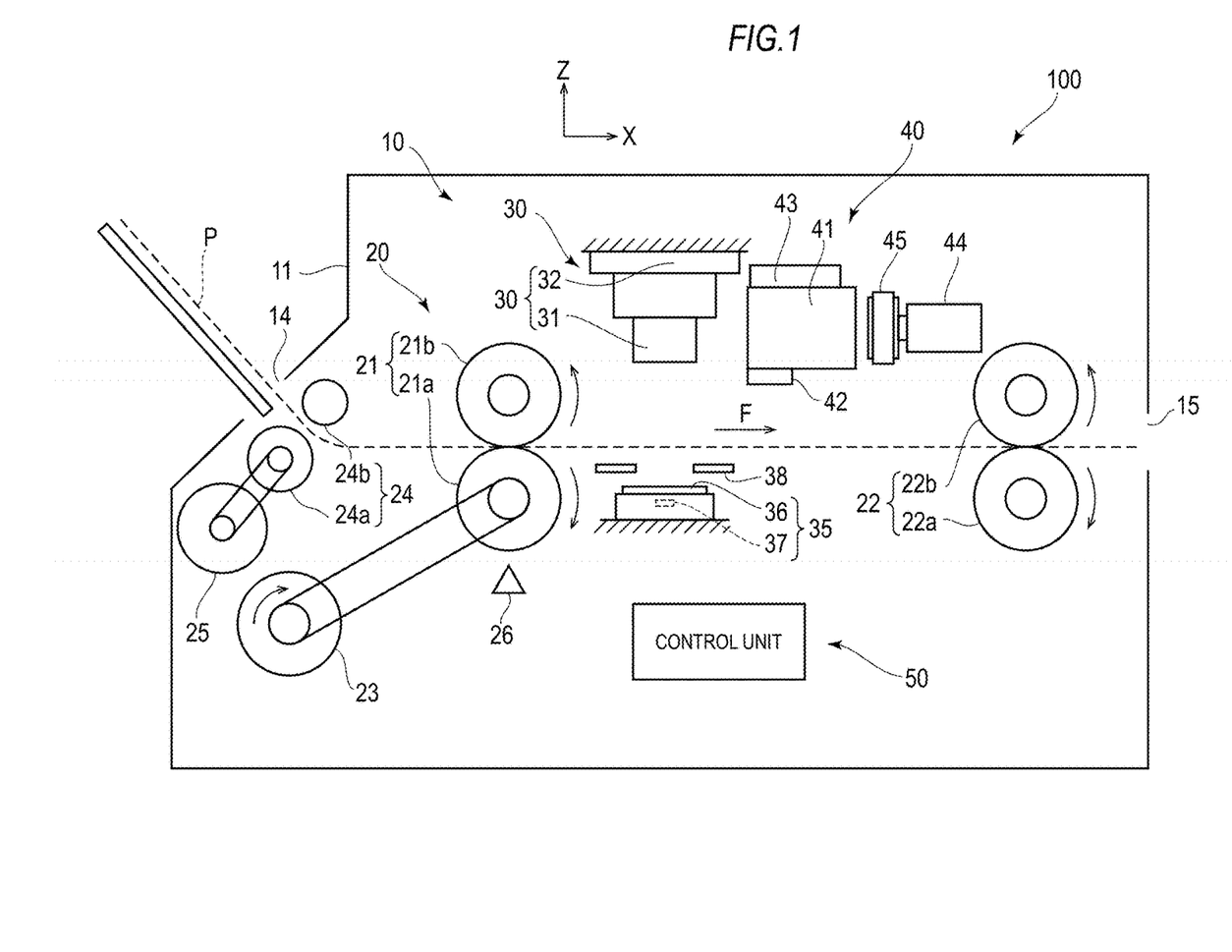
FIG. 1 is a view illustrating a schematic configuration of a recording apparatus 100.

FIG. 1 is a view illustrating a schematic configuration of the recording apparatus 100.

The recording apparatus 100 includes a conveying apparatus 10, a recording unit 40, and a control unit 50 that controls operation of the conveying apparatus 10 and the recording unit 40.

The conveying apparatus 10 conveys a recording medium (hereinafter, called recording paper P) as a fed conveyed object along a conveyance path and discharges the recording medium after the recording medium passes through the recording unit 40. The conveying apparatus 10 includes a housing 11, a conveying unit 20, an imaging unit 30, and a light emitting unit 35.

The housing 11 houses and supports constituent members of the recording apparatus 100. The housing 11 also includes the paper feeding opening 14 for feeding the recording paper P and the paper discharge opening 15 for discharging the recording paper P.

The conveying unit 20 conveys the recording paper P. The conveying unit 20 includes a first conveyor roller unit 21 and a second conveyor roller unit 22 as rotating bodies, a conveyor motor 23, a paper feeding roller unit 24, a paper feeding motor 25, and an encoder 26.

The first conveyor roller unit 21 includes a pair of rollers 21a and 21b and conveys the recording paper P placed between the rollers 21a and 21b. Similarly, the second conveyor roller unit 22 includes a pair of rollers 22a and 22b and conveys the recording paper P placed between the rollers 22a and 22b. The first conveyor roller unit 21 and the second conveyor roller unit 22 are rotatably supported by the housing 11 at positions separated in the conveyance direction. Therefore, a conveyance path of the recording paper P is formed between the pair of rollers 21a and 21b and between the pair of rollers 22a and 22b (the recording paper P and the conveyance path overlap in FIG. 1). The conveyor motor 23 rotates the first conveyor roller unit 21 and the second conveyor roller unit 22. Therefore, the drive of the conveyor motor 23 conveys the recording paper P placed between the pair of rollers 21a and 21b and the pair of rollers 22a and 22b in the conveyance direction (arrow F illustrated in FIG. 1). The paper feeding roller unit 24 includes a pair of rollers 24a and 24b and places the recording paper P between the rollers 24a and 24b. The paper feeding roller unit 24 separates each of a plurality of pieces of recording paper P loaded on a tray and feeds the recording paper P from the paper feeding opening 14. The paper feeding motor 25 rotates the paper feeding roller unit 24. Therefore, the paper feeding motor 25 rotates to feed the recording paper P placed between the pair of rollers 24a and 24b from the paper feeding opening 14. The encoder 26 detects a rotation state by reading a slit along a circumference of a code wheel not illustrated of the first conveyor roller unit 21 and transmits the detected information to the control unit 50.

The conveying unit 20 may be configured to bring the recording paper P into close contact with a conveyor belt to convey the recording paper P instead of conveying the recording paper P by the pairs of rollers.

The imaging unit 30 two-dimensionally images the surface of the recording paper P being conveyed by the conveying unit 20. More specifically, the imaging unit 30 is supported by the housing 11 such that a direction orthogonal to the surface of the recording paper P is an imaging direction. The imaging unit 30 includes a lens 31 and an image sensor 32 including an image pickup element. The imaging unit 30 is arranged on the upstream of the recording unit 40 in the conveyance direction, and the imaging unit 30 images the surface of the recording paper P before the image is recorded by the recording unit 40. The imaging unit 30 transmits the taken image information to the control unit 50.

The imaging range of the imaging unit 30 can include, for example, 1024 pixels×1024 pixels. Assuming that a pitch of one pixel is, for example, 10 μm here, the imaging range is 10.24 mm×10.24 mm. The imaging range can be set to a size according to an amount of conveyance.

The light emitting unit 35 emits light toward the recording paper P from the opposite side of the imaging unit 30. More specifically, the light emitting unit 35 is supported by the housing 11 on the opposite side of the imaging unit 30 across the conveyance path. The light emitting unit 35 includes a lens 36 and a light source 37. An LED can be used for the light source 37, for example. The light emitting unit 35 emits light toward the recording paper P, and the imaging unit 30 images the recording paper P through which the light is transmitted. The conveying apparatus 10 includes light blocking portions 38 between the light emitting unit 35 and the conveyance path. The light blocking portions 38 block light other than the light emitted toward the imaging unit 30 from the light emitting unit 35. Specifically, the light blocking portions 38 block light that illuminates outside of an imaging range described later of the recording paper P in the light emitted from the light emitting unit 35.

The recording unit 40 records an image or the like on the surface of the conveyed recording paper P. The recording unit 40 is arranged on the downstream of the imaging unit 30 in the conveyance direction and is configured to record the image on the recording paper P after the image is taken by the imaging unit 30. The recording unit 40 includes a carriage 41, a recording head 42, an ink tank 43, and a carriage moving motor 44. The carriage 41 is driven by the carriage moving motor 44 to move back and forth in the direction orthogonal to the conveyance direction of the recording paper P and parallel to the surface of the recording paper P, that is, in the Y direction. The recording head 42 discharges ink from a nozzle toward the surface of the recording paper P in conjunction with the backward and forward movement of the carriage 41. The ink tank 43 supplies stored ink to the recording head 42. The carriage moving motor 44 moves the carriage 41 back and forth through a belt 45.

The recording unit 40 is not limited to the inkjet type, and an electrophotographic type, a thermal transfer type, a dot impact type or the like may also be adopted.

The control unit 50 controls the conveying apparatus 10 and the recording unit 40. Specifically, the control unit 50 alternately repeats instructing the conveying apparatus 10 to convey the recording paper P with an amount of conveyance for one step and instructing the recording unit 40 to discharge the ink from the nozzle of the recording head 42 to record an image for one step. Therefore, a process by the conveying apparatus 10 conveying the recording paper P for one step and a process by the recording unit 40 recording an image for one step are repeated in the recording apparatus 100 to record a desired image on the entire surface of the recording paper P.

Figure 2:
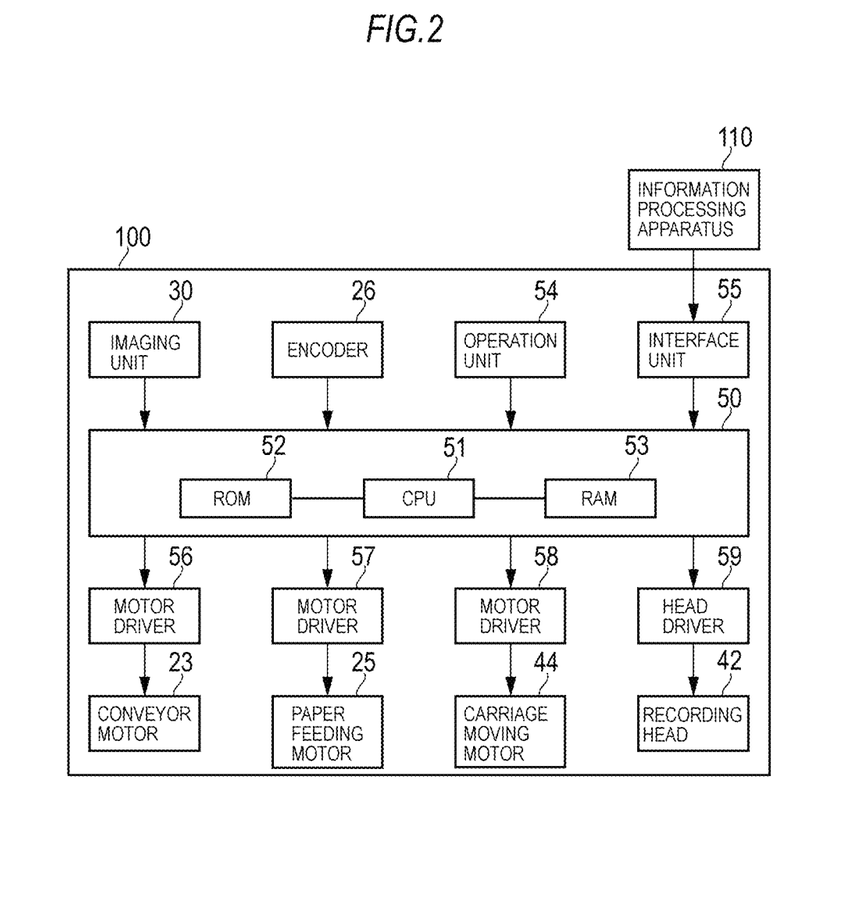
FIG. 2 is a block diagram illustrating an internal configuration of the recording apparatus 100.

FIG. 2 is a block diagram illustrating an internal configuration of the recording apparatus 100 with a focus on the control unit 50.

The control unit 50 includes a CPU 51, a ROM 52, and a RAM 53 and functions as a so-called computer.

The CPU 51 expands a program stored in the ROM 52 to the RAM 53 and executes the program to control the entire recording apparatus 100. The program and data necessary for a process by the CPU 51 are stored in the ROM 52. The RAM 53 is a memory that temporarily stores information when the CPU 51 executes the process.

The control unit 50 is connected to the imaging unit 30, the encoder 26, an operation unit 54, and an information processing apparatus 110 and is configured to receive information from them. A user operates the operation unit 54 to issue an instruction to the control unit 50. Examples of the operation unit 54 include a switch, a button, and a touch panel. Examples of the information processing apparatus 110 include a PC, a smartphone, and a tablet terminal, and the information processing apparatus 110 is connected in a wireless or wired manner through an interface unit 55.

The control unit 50 is connected to the conveyor motor 23, the paper feeding motor 25, the carriage moving motor 44, and the recording head 42 through motor drivers 56, 57, and 58 and a head driver 59, respectively, and is configured to transmit information to them.

In the recording apparatus 100 configured as described above, the imaging unit 30 images, at different timings, the recording paper P being conveyed and transmits the taken image information to the control unit 50. Based on two pieces of image information taken at different timings, the control unit 50 uses pattern matching to detect actual conveyance information of the recording paper P, specifically, a distance conveyed in the X direction and a distance conveyed in the Y direction (specifically, distance displaced in the Y direction). Therefore, the control unit 50 functions as a conveyance detection apparatus that detects conveyance information. The control unit 50 also controls the recording head 42 to discharge the ink according to the detected actual conveyance information. Therefore, the recording unit 40 can record an image without a break and without an overlap.

As described, the conveying apparatus 10 of the present embodiment includes the light emitting unit 35 on the opposite side of the imaging unit 30 across the conveyance path, and the light emitting unit 35 emits light toward the recording paper P. Therefore, the imaging unit 30 images the recording paper P through which the light is transmitted. In this case, the light reflected by unevenness on the back surface of the recording paper P in the light emitted from the light emitting unit 35 is reflected in various directions, and the light transmitted through the recording paper P goes straight toward the imaging unit 30. Therefore, the imaging unit 30 can mainly image the light transmitted through the recording paper P and going straight toward the imaging unit 30. As a result, the effect of the unevenness on the surface of the recording paper P can be reduced in the imaging, compared to when the light is applied to the surface of the recording paper P from obliquely above.

The imaging unit 30 can image the recording paper P through which the light is transmitted and can take a two-dimensional image with less perspective. The image with less perspective here denotes an image in which the same subject comes out in substantially the same way when the subject is positioned at the center of the imaging range and when the subject is positioned apart from the center of the imaging range. When the pattern matching is used to detect the conveyance information of the recording paper P from two pieces of image information obtained by imaging the conveyed recording paper P at different timings, the image with less perspective can be used to improve the accuracy of the pattern matching. A telecentric lens is usually used for the lens of the imaging unit 30 to take the image with less perspective. The telecentric lens is a lens designed such that the principal ray is parallel to the lens optical axis. However, the telecentric lens is more expensive than a non-telecentric lens, and the manufacturing cost of the imaging unit 30 is increased when the telecentric lens is used. Therefore, the recording paper P through which the light is transmitted can be imaged as described above to take a two-dimensional image with less perspective even when the non-telecentric lens is used for the lens 31 of the imaging unit 30, just like when the telecentric lens is used.

The following verifies the fact that the image with less perspective can be taken when the light is transmitted from below the recording paper.

(First Verification)

Images taken by using the non-telecentric lens and the telecentric lens when the light is applied from above the recording paper and when the light is transmitted from below the recording paper will be compared here. The following FIGS. 3A to 3D illustrate images obtained by photographing the same region of the recording paper.

Figure 3A:
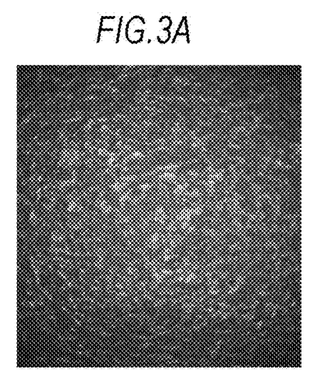
FIGS. 3A to 3D are views illustrating images obtained by photographing recording paper P.

FIG. 3A illustrates an image taken by applying the light from above the recording paper and using a macro lens as the non-telecentric lens.

Figure 3B:
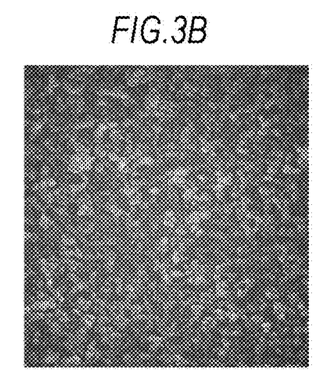

FIG. 3B illustrates an image taken by applying the light from above the recording paper and using the telecentric lens.

The image taken by using the non-telecentric lens in FIG. 3A is perspective, and the image is different from the image taken by using the telecentric lens in FIG. 3B when the light is applied from above the recording paper.

Figure 3C:
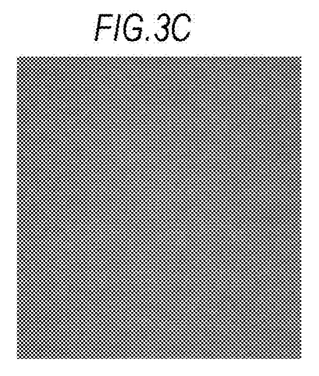

FIG. 3C illustrates an image taken by transmitting the light from below the recording paper and using the macro lens as the non-telecentric lens.

Figure 3D:
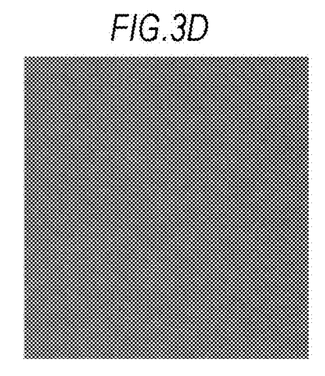

FIG. 3D illustrates an image taken by transmitting the light from below the recording paper and using the telecentric lens.

There is substantially no change between the image taken by using the non-telecentric lens in FIG. 3C and the image taken by using the telecentric lens in FIG. 3D when the light is transmitted from below the recording paper. In this way, when the light is transmitted from below the recording paper, an image with reduced perspective can be taken even if the non-telecentric lens is used.

(Second Verification)

Next, images taken by using the non-telecentric lens when the light is applied from above the recording paper provided with a predetermined pattern and when the light is transmitted from below will be compared.

Figure 4A:
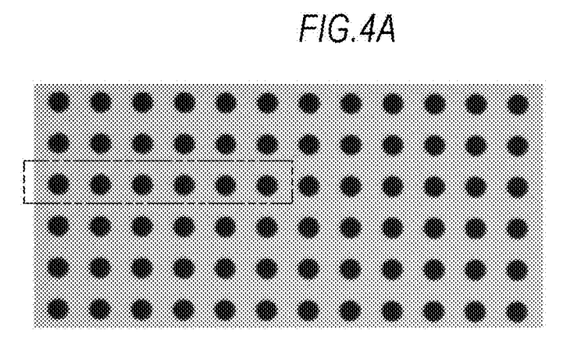
FIGS. 4A to 4D are views of a pattern with black circles and binary images of images obtained by photographing the pattern with black circles.

FIG. 4A is a view illustrating the recording paper provided with a pattern including the same black circles arranged at constant intervals.

Figure 4B:
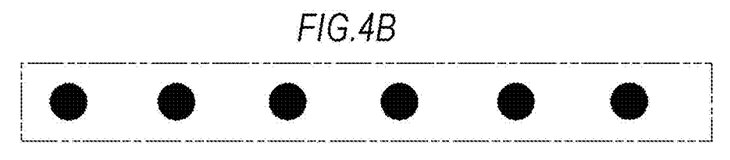

FIG. 4B is a view of a binary image of an image taken by applying the light to the recording paper of FIG. 4 from above and using the telecentric lens. Here, an image of a range indicated by an alternate long and two short dashes line in FIG. 4A is binary. As illustrated in FIG. 4B, there is no change in the shape of the black circles near the center and near the end of the recording paper.

Figure 4C:
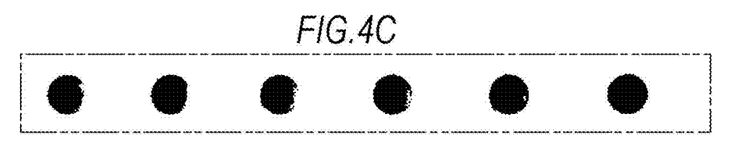

FIG. 4C is a view of a binary image of an image taken by applying the light to the recording paper of FIG. 4A from above and using the macro lens as the non-telecentric lens. As in FIG. 4B, the image of the range indicated by the alternate long and two short dashes line in FIG. 4A is binary. The image is perspective in FIG. 4C, and the shape of the black circles can be reproduced near the center of the recording paper. However, the shape of the black circles is broken near the end.

Figure 4D:
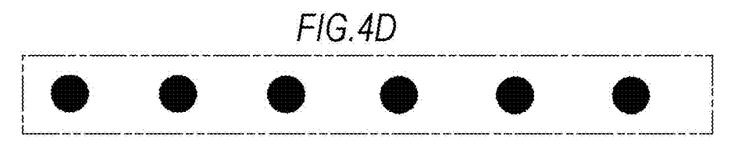

FIG. 4D is a view of a binary image of an image taken by transmitting the light from below the recording paper of FIG. 4A and using the macro lens as the non-telecentric lens. As in FIG. 4B, the image of the range indicated by the alternate long and two short dashes line in FIG. 4A is binary. The perspective is reduced in FIG. 4D, and the shape of the black circles is reproduced near the center and near the end of the recording paper. Therefore, as in FIG. 4B, there is no change in the shape of the black circles near the center and near the end of the recording paper in FIG. 4D.

When the light is transmitted from below the recording paper, there is substantially no change between the image of FIG. 4D taken by using the non-telecentric lens and the image of FIG. 4B taken by using the telecentric lens. In this way, when the light is transmitted from below the recording paper, an image with reduced perspective can be taken even if the non-telecentric lens is used.

Figure 5:
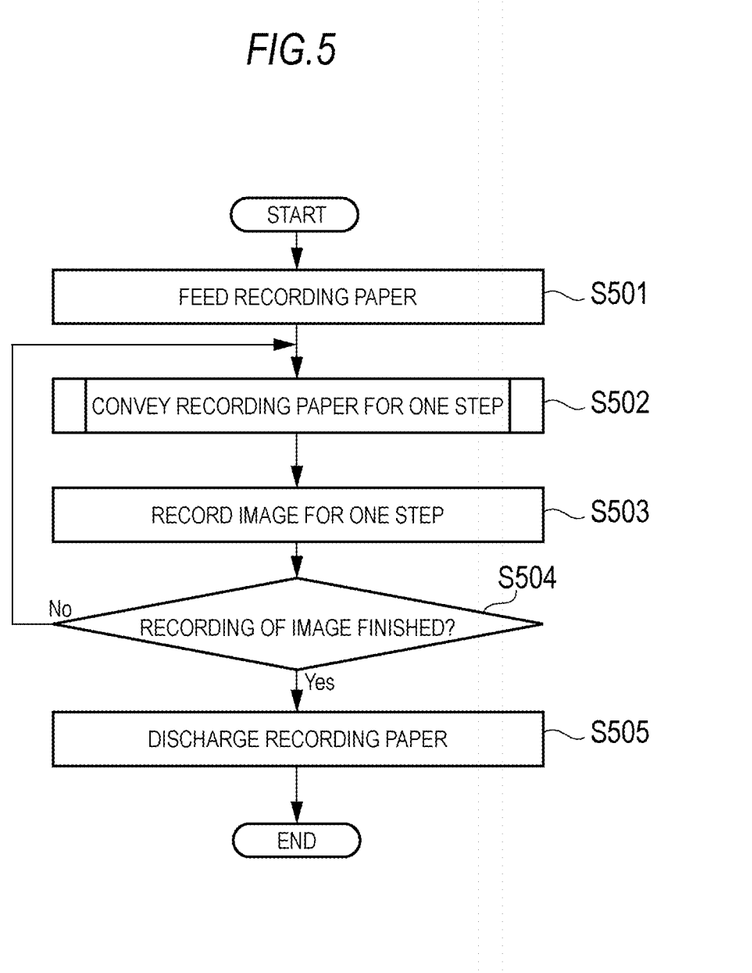
FIG. 5 is a flow chart illustrating a process by a control unit 50.
Figure 6:
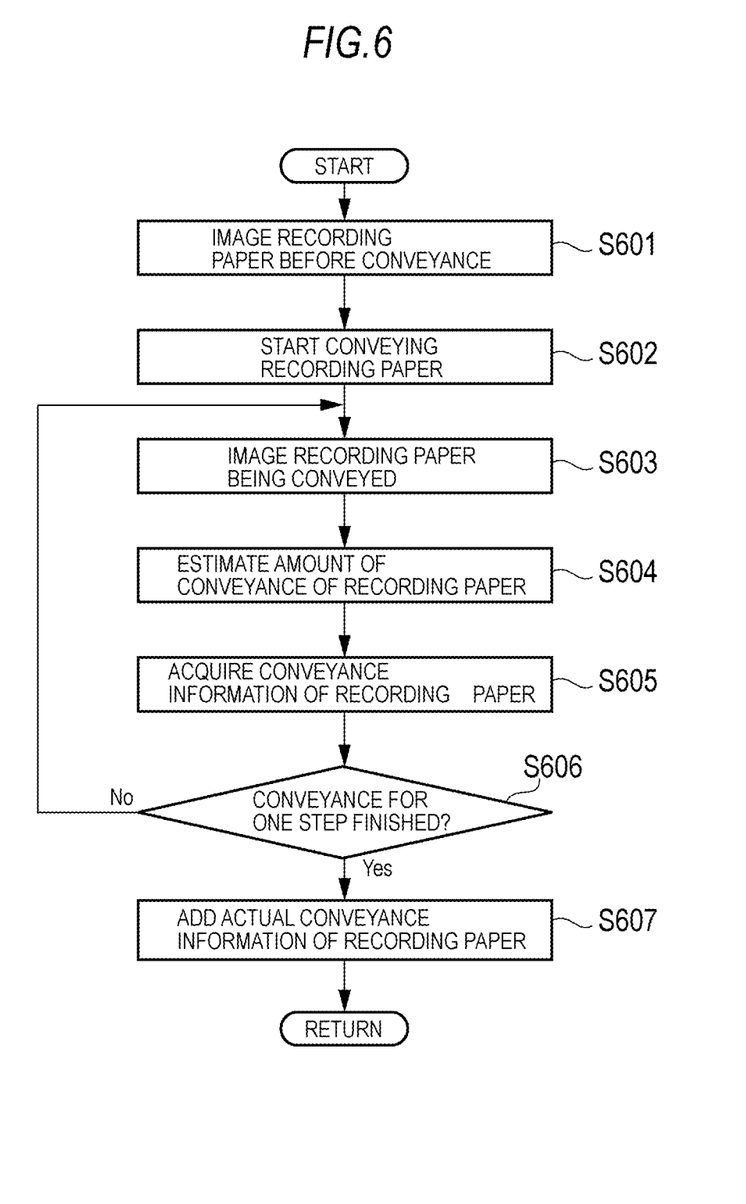
FIG. 6 is a flow chart illustrating a process by the control unit 50.

Next, a process by the control unit 50 detecting the conveyance information of the recording paper P will be described with reference to flow charts of FIGS. 5 and 6. The CPU 51 of the control unit 50 expands a program stored in the ROM 52 to the RAM 53 and executes the program to realize the flow charts of FIGS. 5 and 6.

In S501, the control unit 50 drives the paper feeding motor 25 to rotate the paper feeding roller unit 24 and separates each of the plurality of pieces of recording paper P loaded on the tray to feed the recording paper P from the paper feeding opening 14. The control unit 50 further sets a desired position for the recording paper P and drives the conveyor motor 23 to convey the recording paper P to a recording start position.

In S502, the control unit 50 drives the conveyor motor 23 to convey the recording paper P for one step. Based on the image information taken by the imaging unit 30, the control unit 50 also detects the conveyance information of the recording paper P actually conveyed at the conveyance of the recording paper P for one step, more specifically, the distance conveyed in the X direction and the distance conveyed in the Y direction. Details of the process will be described later with reference to the flow chart of FIG. 6.

In S503, the control unit 50 drives the carriage moving motor 44 to move the carriage 41 and discharges the ink from the nozzle of the recording head 42 to record the image for one step in which the recording paper P is conveyed.

In this case, the control unit 50 controls the recording head 42 to discharge the ink according to the detected actual conveyance information. Specifically, based on the actual distance conveyed in the X direction, the control unit 50 records the image throughout a region equivalent to the distance conveyed in the X direction. For example, when the distance actually conveyed is longer than the original amount of conveyance in the X direction, the image is recorded for a region including the extra length in the X direction. The control unit 50 also makes an offset equivalent to the distance conveyed in the Y direction (distance displaced in the Y direction) and records the image. Although the conveying unit 20 is not ordinarily supposed to convey the recording paper P in the Y direction, the recording paper P may be displaced in the Y direction due to slipping of the conveyor roller unit or the like. In this case, the control unit 50 records the image by shifting the timing of the start of the discharge of the ink according to the distance conveyed in the Y direction when the control unit 50 moves the recording head 42 in the Y direction.

In S504, the control unit 50 determines whether all of the recording of the image is finished. If all of the recording of the image is finished, the control unit 50 proceeds to step S505. If all of the recording of the image is not finished, the control unit 50 returns to S502 to repeat the process of S502 and S503.

In S505, the control unit 50 drives the conveyor motor 23 to discharge the recording paper P with the recorded image from the paper discharge opening 15.

Next, the process of S502 will be described with reference to the flow chart of FIG. 6.

In S601, the control unit 50 instructs the imaging unit 30 to take an image before the recording paper P is conveyed from the recording start position. The imaging unit 30 images, in the imaging range, the recording paper P through which the light is transmitted from below and transmits the taken image information, that is, image data, to the control unit 50. The control unit 50 applies image processing, such as shading correction, to the received image data and stores the image data after the image processing. In this case, the control unit 50 stores the image data after adding identification information to the image data. For the convenience, the stored image data will be called first image data here.

Figure 7:
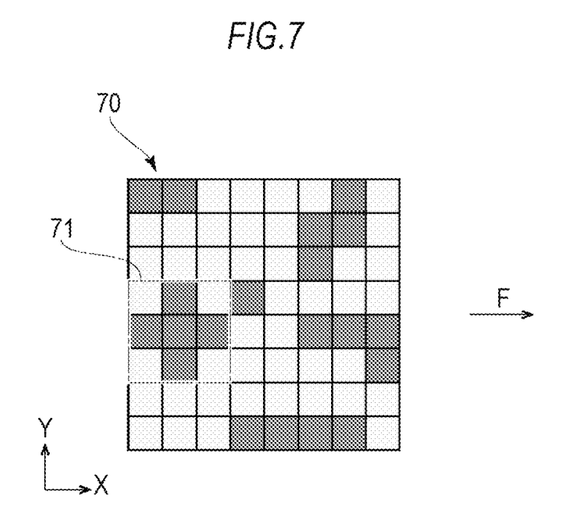
FIG. 7 is a view illustrating an example of first image data 70 imaged by the imaging unit 30.

FIG. 7 is a view illustrating an example of first image data 70 imaged by the imaging unit 30. Each rectangle in the first image data 70 illustrated in FIG. 7 indicates one pixel of the image pickup element of the imaging unit 30. To facilitate the understanding, it is assumed here that the imaging range is a range of 8 pixels×8 pixels, and the image is a gray scale image with 256 black and white gradations.

As illustrated in FIG. 7, the first image data 70 indicates an image obtained by imaging the recording paper P through which the light is transmitted from below. Due to the unevenness on the front surface and the back surface, the recording paper P includes parts where the light is easily transmitted and parts where the light is not easily transmitted. Therefore, a pattern with different brightness values emerges in the image obtained by imaging the recording paper P. The control unit 50 extracts an image of a predetermined region (region in an alternate long and short dash line) as a template image 71 and stores brightness information and position information. For example, the control unit 50 stores the brightness value of each pixel in the template image 71 and the center coordinates of the template image 71 in the first image data 70. In FIG. 7, the center coordinates of the template image 71 are (X, Y)=(2, 4).

In S602, the control unit 50 instructs the conveyor motor 23 to start conveying the recording paper P by an amount of conveyance for one target step (hereinafter, called a target amount of conveyance). Therefore, the conveyor motor 23 rotates the first conveyor roller unit 21 to convey the recording paper P for the target amount of conveyance.

In S603, the control unit 50 instructs the imaging unit 30 to image the recording paper P being conveyed. In the same imaging range as in S601, the imaging unit 30 takes an image of the recording paper P conveyed while the light is transmitted from below, and the imaging unit 30 transmits the taken image data to the control unit 50. The control unit 50 applies image processing, such as shading correction, to the received image data and stores the image data after the image processing. In this case, the control unit 50 stores the image data after adding identification information to the image data. For the convenience, the stored image data will be called second image data here.

Figure 8:
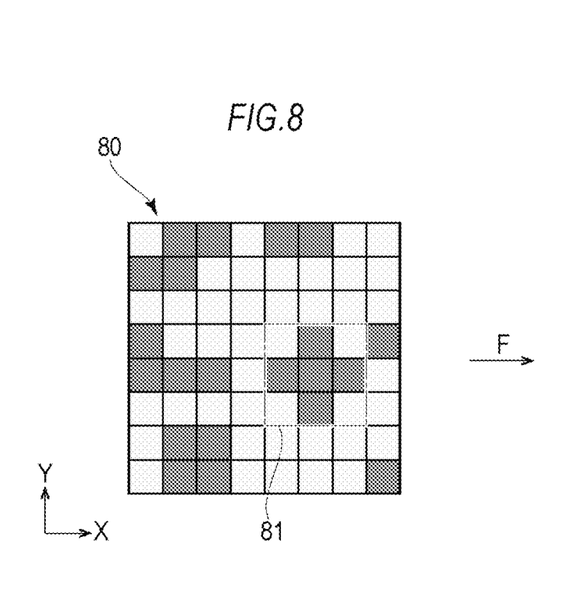
FIG. 8 is a view illustrating an example of second image data 80 imaged by the imaging unit 30.

FIG. 8 is a view illustrating an example of second image data 80 imaged by the imaging unit 30. As illustrated in FIG. 8, in the second image data 80, a region equivalent to the template image 71 of the first image data 70 is moved in the conveyance direction.

The timing of imaging in S603 is set in a time period (predetermined time) in which the second image data 80 includes the region equivalent to the template image 71 of the first image data 70. The predetermined time is stored in advance in the control unit 50 based on the imaging range and the conveyance speed.

In S604, the control unit 50 estimates an amount of conveyance of the recording paper P between the imaging of the last time and the imaging of this time. Specifically, the control unit 50 calculates the amount of conveyance of the recording paper P (hereinafter, called an estimated amount of conveyance) from the information detected by the encoder 26. The estimated amount of conveyance is detected based on the amount of rotation of the first conveyor roller unit 21 and is different from the actual amount of conveyance of the recording paper P when the first conveyor roller unit 21 is decentered or when there is slipping between the first conveyor roller unit 21 and the recording paper P. The control unit 50 stores the calculated estimated amount of conveyance.

In S605, the control unit 50 acquires the actual conveyance information of the recording paper P from the first image data 70 and the second image data 80. The process is an example of the process by the conveyance detection unit.

Specifically, the control unit 50 acquires the actual conveyance information of the recording paper P by searching the position of the pattern image, which is similar to the template image 71 extracted from the first image data 70, in the second image data 80.

Here, a pattern matching method can be used as a method of searching the position of the pattern image similar to the template image 71. As illustrated in FIG. 8, the control unit 50 uses, for example, SAD (Sum of Absolute Difference) to search the pattern image similar to the template image 71 from the second image data 80 based on the brightness information of each image. In this case, the control unit 50 can quickly perform the pattern matching by searching only the proximity of the estimated amount of conveyance based on the estimated amount of conveyance calculated in S604. The control unit 50 specifies a pattern image 81 most similar to the template image 71 and acquires the position information of the specified pattern image 81. In FIG. 8, the coordinates (center coordinates) of the pattern image 81 are (X, Y)=(6, 4).

Next, the control unit 50 calculates the actual conveyance information by obtaining the difference in the X direction and the difference in the Y direction from the coordinates of the template image 71 of the first image data 70 and the coordinates of the specified pattern image 81. In FIGS. 7 and 8, the control unit 50 can acquire the conveyance information indicating that the recording paper P is conveyed +4 pixels in the X direction and 0 pixels in the Y direction based on the difference in the coordinates. The control unit 50 stores the acquired actual conveyance information.

In S606, the control unit 50 determines whether the conveyance equivalent to one step is finished. If the conveyance equivalent to one step is not finished, the control unit 50 returns to S603 to repeat the process from S603 to S605. In this case, the control unit 50 sets, as the second image data, new image data acquired by returning to S603 and sets, as the first image data, the image data acquired in S603 of the last time to execute the process from S603 to S605. More specifically, in S603, it is preferable that the control unit 50 extracts the predetermined region as the template image 71 as in S601 and stores the brightness information and the position information, in addition to the storage of the image data after the image processing.

On the other hand, if the conveyance equivalent to one step is finished, the control unit 50 proceeds to S607. The control unit 50 proceeds to S607 when the conveyance is temporarily halted for the recording of the image by the recording unit 40 after the end of the conveyance equivalent to one step.

In S607, the control unit 50 adds all the actual conveyance information stored in S605 to acquire the conveyance information of the recording paper P actually conveyed in the conveyance for one step. Specifically, the control unit 50 adds the pixels in the X direction and the Y direction and multiplies the added pixels by the pixel pitch to acquire the distance conveyed in the X direction and the distance conveyed in the Y direction.

In this way, the control unit 50 can acquire the conveyance information of the recording paper P actually conveyed in the conveyance for one step to control the recording head 42 according to the detected actual conveyance information to discharge the ink in S503. Therefore, the control unit 50 records the image throughout the region equivalent to the distance conveyed in the X direction based on the actual distance conveyed in the X direction and records the image after offsetting the image according to the distance displaced in the Y direction. This can prevent a broken image and an overlapped image even when the recording unit 40 records the image step by step.

According to the present embodiment, the conveying apparatus 10 includes the light emitting unit 35 arranged on the opposite side of the imaging unit 30 across the conveyance path. The imaging unit 30 images the recording paper P through which the light from the light emitting unit 35 is transmitted while the recording paper P is conveyed. In this case, the imaging unit 30 can mainly image the light transmitted through the recording paper P and going straight toward the imaging unit 30, and the imaging unit 30 can take an image with reduced effect of the unevenness on the surface of the recording paper P. Reducing the effect of the unevenness can prevent the template image from changing before and after the conveyance of the recording paper P for a predetermined distance when the recording paper P is imaged. Therefore, highly accurate conveyance information can be detected by detecting the conveyance information of the recording paper P based on the image information with the reduced effect of the unevenness.

When the light is applied to the surface of the recording paper P from obliquely above, the taken image exhibits blow-out highlights if the recording paper P is paper with a high light reflectance such as glossy paper, and it is difficult to detect the conveyance information. On the other hand, according to the present embodiment, the imaging unit 30 images the recording paper P through which the light from the light emitting unit 35 is transmitted while the recording paper P is conveyed. Therefore, the light is not reflected by the surface of the recording paper P, and the conveyance information can be detected even when the recording paper P is glossy paper or the like.

According to the present embodiment, the light is transmitted from below the recording paper P, and an image with reduced perspective can be taken even when the non-telecentric lens is used. Therefore, the imaging unit 30 can use the non-telecentric lens, and the manufacturing cost of the imaging unit 30 can be reduced.

According to the present embodiment, the conveying apparatus 10 includes the light blocking portions 38 between the conveyance path and the light emitting unit 35, wherein the light blocking portions 38 block the light other than the light emitted toward the imaging unit 30. This can prevent the light not going toward the imaging unit 30 from being reflected by other members and imaged by the imaging unit 30.

Although the present invention has been described with reference to the embodiment, the present invention is not limited to the embodiment, and changes can be made within the scope of the present invention.

In the case described in the embodiment, the process from S603 to S605 is repeated, and the conveyance information of the recording paper P actually conveyed for one step is acquired in S607. The recording unit 40 records the image based on the acquired conveyance information. However, the present invention is not limited to this. For example, the actual conveyance information may be acquired in S605, and the acquired actual conveyance information may be fed back to control the conveyor motor 23 in real time. More specifically, the control unit 50 controls the conveyor motor 23 to reduce the amount of rotation when the acquired actual conveyance information is long and controls the conveyor motor 23 to increase the amount of rotation when the acquired actual conveyance information is short. Therefore, when the conveyance for one step is finished, the same amount of conveyance as the scheduled amount of conveyance for one step can be conveyed. As a result of the control, the recording unit 40 only has to always record the image for one step, and the control unit 50 can reduce the control for the recording unit 40. As a result of the control, the printer is not limited to the inkjet type in which the image is recorded step by step, and a printer of an electrophotographic type, a thermal transfer type, a dot impact type, or the like can also be used. As a result of the control, not only the recording apparatus 100, but also a conveying apparatus without the configuration of the recording unit 40 can be adopted. Note that an example of the conveying apparatus includes an image reading apparatus, such as a scanner, in which the configuration of the recording unit 40 is replaced with a configuration of an image reading unit.

Although the control unit 50 is arranged in the housing 11 in the case described in the present embodiment, the present invention is not limited to the case, and the control unit 50 may be arranged outside of the housing 11. In this case, the control unit 50 can control the conveying apparatus 10 and the recording unit 40 in a wired or wireless manner.

Although the CPU 51 executes the program to realize the process in the case described in the present embodiment, the present invention is not limited to the case, and each circuit including hardware may execute the process.

The present invention also includes the program and a computer-readable recording medium recording the program.

According to the present invention, highly accurate conveyance information can be detected.

It should be noted that the above embodiments merely illustrate concrete examples of implementing the present invention, and the technical scope of the present invention is not to be construed in a restrictive manner by these embodiments. That is, the present invention may be implemented in various forms without departing from the technical spirit or main features thereof.

What is claimed is:

1. A conveyance detection apparatus of a conveying apparatus, the conveying apparatus comprising:
   a conveying unit that conveys a conveyed object along a conveyance path;
   an imaging unit that images the conveyed object; and
   a light emitting unit arranged on an opposite side of the imaging unit across the conveyance path, the conveyance detection apparatus comprising
   a conveyance detection unit that detects conveyance information of the conveyed object based on image information of the conveyed object imaged by the imaging unit in a state in which light from the light emitting unit is transmitted through the conveyed object, wherein
   the conveyance detection unit detects the conveyance information of the conveyed object based on a plurality of images of the conveyed object imaged at different timings by the imaging unit.

2. The conveyance detection apparatus of the conveying apparatus according to claim 1, wherein
   the imaging unit comprises a lens, and
   the lens is a non-telecentric lens.

3. The conveyance detection apparatus of the conveying apparatus according to claim 1, wherein
   the plurality of images include images of a same part of the conveyed object.

4. The conveyance detection apparatus of the conveying apparatus according to claim 1, wherein
   the conveying apparatus comprises
   a light blocking portion between the conveyance path and the light emitting unit, wherein the light blocking portion blocks light other than light emitted toward the imaging unit.

5. The conveyance detection apparatus of the conveying apparatus according to claim 1, wherein
   the conveying apparatus comprises
   a housing that houses the conveying unit, the imaging unit, and the light emitting unit.

6. A conveying apparatus comprising:
   a conveying unit that conveys a conveyed object along a conveyance path;
   an imaging unit that images the conveyed object;
   a light emitting unit arranged on an opposite side of the imaging unit across the conveyance path;
   a conveyance detection unit that detects conveyance information of the conveyed object based on image information of the conveyed object imaged by the imaging unit in a state in which light from the light emitting unit is transmitted through the conveyed object; and a housing that houses the conveying unit, the imaging unit, and the light emitting unit, wherein the conveyance detection unit detects the conveyance information of the conveyed object based on a plurality of images of the conveyed object imaged at different timings by the imaging unit.

7. A recording apparatus comprising:

a conveying unit that conveys a conveyed object along a conveyance path;

an imaging unit that images the conveyed object;

a light emitting unit arranged on an opposite side of the imaging unit across the conveyance path;

a conveyance detection unit that detects conveyance information of the conveyed object based on image information of the conveyed object imaged by the imaging unit in a state in which light from the light emitting unit is transmitted through the conveyed object; and a recording unit that records an image based on the conveyance information detected by the conveyance detection unit, wherein the conveyance detection unit detects the conveyance information of the conveyed object based on a plurality of images of the conveyed object imaged at different timings by the imaging unit.

* * * * *